United States Patent
Denison et al.

(10) Patent No.: US 9,358,139 B2
(45) Date of Patent: Jun. 7, 2016

(54) EXPANDABLE DEVICES

(75) Inventors: Andy Edward Denison, Temecula, CA (US); Kent C. B. Stalker, San Marcos, CA (US); Mark Bates, Encinitas, CA (US)

(73) Assignee: CELONOVA BIOSCIENCES, INC., San Antonio, TX (US)

( * ) Notice: Subject to any disclaimer, the term of this patent is extended or adjusted under 35 U.S.C. 154(b) by 443 days.

(21) Appl. No.: 13/819,846

(22) PCT Filed: Aug. 30, 2011

(86) PCT No.: PCT/US2011/049804
§ 371 (c)(1),
(2), (4) Date: Sep. 27, 2013

(87) PCT Pub. No.: WO2012/030871
PCT Pub. Date: Mar. 8, 2012

(65) Prior Publication Data
US 2014/0012364 A1  Jan. 9, 2014

Related U.S. Application Data

(60) Provisional application No. 61/378,330, filed on Aug. 30, 2010.

(51) Int. Cl.
*A61F 2/915* (2013.01)
*A61F 2/82* (2013.01)

(52) U.S. Cl.
CPC . *A61F 2/82* (2013.01); *A61F 2/915* (2013.01); *A61F 2002/91525* (2013.01); *A61F 2002/91541* (2013.01); *A61F 2002/91558* (2013.01); *A61F 2230/0054* (2013.01)

(58) Field of Classification Search
CPC ............ A61F 2/915; A61F 2250/0029; A61F 2250/0036; A61F 2002/91525; A61F 2002/91541
See application file for complete search history.

(56) References Cited

U.S. PATENT DOCUMENTS 6,579,310 B1 * 6/2003 Cox et al. .................. 623/1.16
8,105,373 B2 * 1/2012 Girton et al. ............... 623/1.15

(Continued)

FOREIGN PATENT DOCUMENTS

DE  102007019772 A1  10/2008
WO  WO9915108 A2  4/1999

(Continued)

OTHER PUBLICATIONS

PCT/US2011/049804 International Search Report.

*Primary Examiner* — David Isabella
*Assistant Examiner* — Suba Ganesan
(74) *Attorney, Agent, or Firm* — Mannava & Kang, P.C.; Carol L. Bunner

(57) ABSTRACT

An expandable, bistable open cell design incorporates the following features: a first relatively stiff portion (152) having first and second ends and a first relatively flexible portion (154) connected to the first and second ends of the first relatively stiff portion, the first relatively stiff portion and the first relatively flexible portion substantially surrounding a first open area (156) of the stent structure; a second relatively stiff portion (158) having first and second ends and a second relatively flexible portion (160) connected to the first and second ends of the first relatively stiff portion, the first relatively stiff portion and the first relatively flexible portion substantially surrounding a second open area (162) of the stent structure; and an opening (110) formed through the first relatively stiff portion and the second relatively flexible portion such that the opening connects the first and second open areas, thereby creating first and second intermediate ends (152a, 152b) of the first relatively stiff portion and first and second intermediate ends (160a, 160b) of the second relatively flexible portion. The first intermediate end (152a) of the relatively stiff portion is connected to the first intermediate end (160a) of the relatively flexible portion so as to create a first inward apex (170), the second intermediate end (152b) of the relatively stiff portion is connected to the second intermediate end (160b) of the relatively flexible portion so as to create a second inward apex (172), and the stent structure is configured such that, in a collapsed configuration, the first inward apex (170) is in contact with the second inward apex (172) and, in an expanded configuration, the first inward apex is biased to move in a first circumferential direction and the second inward apex is biased to move in a second circumferential direction that is different than the first circumferential direction.

16 Claims, 7 Drawing Sheets

(56) References Cited

U.S. PATENT DOCUMENTS

2003/0176914 A1 9/2003 Rabkin et al.
2005/0004650 A1 1/2005 Oepen et al.

FOREIGN PATENT DOCUMENTS

| WO | WO9939660 A1 | 8/1999 |
| WO | WO2008049120 A1 | 4/2008 |

* cited by examiner

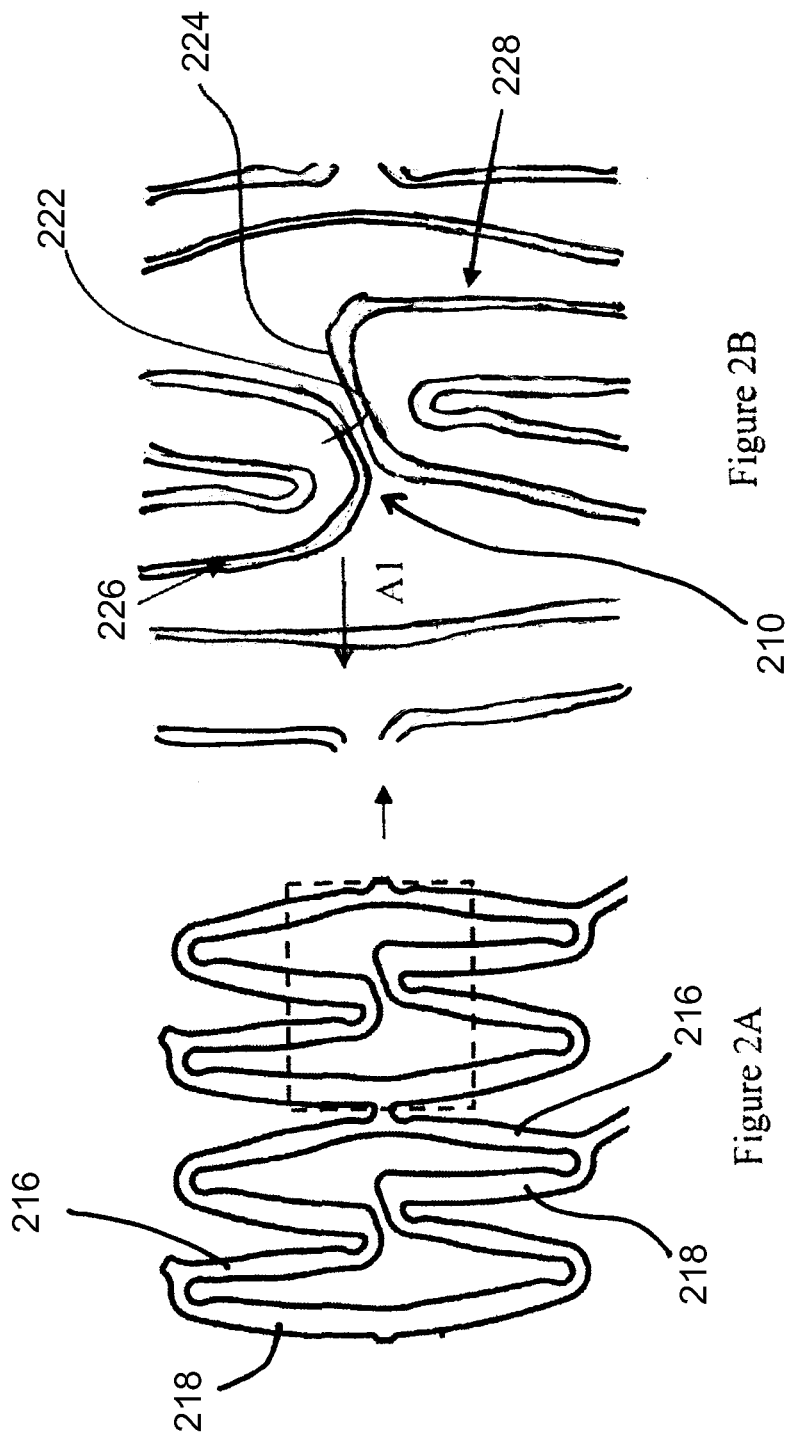

EXPANDABLE DEVICES

CROSS-REFERENCE TO RELATED APPLICATIONS

This application is a national phase application of PCT/US2011/049804, filed Aug. 30, 2011, which claims the benefit of priority to U.S. Provisional Patent Application No. 61/378,330, having a filing date of Aug. 30, 2010, the disclosures of which are incorporated herein by reference in their entirety.

U.S. Pat. No. 6,488,702, filed on Jan. 23, 1998, entitled BISTABLE SPRING CONSTRUCTION FOR A STENT AND OTHER MEDICAL APPARATUS, and U.S. patent application Ser. No. 11/875,718, filed on Sep. 19, 2007, entitled DEFORMABLE LUMEN SUPPORT DEVICES AND METHODS OF USE, are hereby incorporated by reference in their entireties as if fully set forth herein.

TECHNICAL FIELD

The present disclosure relates to expandable devices, such as, for example, stents, other medical devices, and other medical and non-medical lumen support devices. More particularly, to expandable devices having open cells.

BACKGROUND

The present disclosure relates to expandable devices for use in supporting a passageway. While not limited to medical applications only, this disclosure specifically contemplates medical uses such as a vascular prosthesis, commonly referred to as s stent.

Stents are now widely used in interventional cardiovascular procedures for treating narrowed regions within coronary arteries, and other vessels. Such stent devices generally have a tubular shape and are deployed in a vessel to restore and maintain the patency of a segment of a vessel which has become partially occluded by plaque, and is deployed into the vessel after the occluded region has been re-opened by use of a catheter having an expandable dilatation balloon.

Until recently, previously-known vascular stent prostheses have been either "self-expanding" or "plastically-deformable" devices. While stents are frequently deployed after performing a percutaneous transluminal coronary angioplasty (PTCA) procedure to dilate occluded coronary arteries, efforts have also been made to use such stent devices for treatment of occlusive peripheral vascular disease, such as for carotid arteries, renal arteries and superficial femoral arteries. However, stents used for such peripheral applications frequently require a different set of structural characteristics than those typically used in cardiac stenting. The present disclosure offers several improvements over self-expanding and plastically-deformable stents, not only with respect to the flexibility of the stent implant over known devices, but also as to improved ease of delivery and deployment.

U.S. Pat. No. 4,733,665 to Palmaz discloses two types of plastically-deformable stents (e.g., stents typically formed of relatively inelastic metals, such as stainless steel, cobalt chromium, etc.), which are delivered within the vasculature via a balloon catheter, onto which the stent is mounted for deployment by balloon expansion. The stents described in Palmaz are constructed from a wire mesh tube or a slotted metal tube. These stents are crimped around the deflated balloon of a delivery catheter to prevent premature release from the catheter while being introduced into the vessel location being treated. Deployment of these stents is accomplished by inflating the balloon at high pressure to expand the tubular device to a predetermined diameter through plastic deformation until it approximates the desired dimension of the patent vascular lumen being treated. Since plastically-deformable stents are typically formed of relatively inelastic metal alloys (such as stainless steel or cobalt chromium), they tend to provide less flexibility than self-expanding stents formed of more elastic materials (such as nitinol). Consequently, plastically-deformable stents are considered generally inappropriate for deployment into blood vessels that are subject to recurring forces associated with compression and elongation, as well as torsional forces, or other forms of dynamic loading. While plastically-deformable stents generally provide adequate radial strength, such stents typically also have a high degree of axial rigidity. Thus, plastically-deformable stents should not be employed in vessels that routinely experience longitudinal shape changes, because the stents lack flexibility to conform to the vessel, and may fracture, deform or cause dissection of the vessel.

Over the past several years, much effort has been expended attempting to design plastically-deformable stents having strut arrangements with flexible axial connectors or links which permit adjacent circumferential rings of a plastically-deformable stent to provide improved longitudinal flexibility, so that the stent will more readily bend and articulate to conform to the particular shape of a vessel during delivery and upon implant. Examples of various plastically-deformable stents with improved articulating properties are found in U.S. Pat. No. 5,195,984 to Schatz, U.S. Pat. No. 5,514,154 to Lau et al., and U.S. Pat. No. 6,723,119 to Pinchasik et al. However, reliance upon such articulating links does not entirely solve the issues with respect to fatigue and fracture. In other words, plastically-deformable stents typically incorporate metal alloys which are inherently limiting with respect to the amount of bending tolerated before the material work-hardens and fractures. Plastically-deformable stents not only suffer from the above limitations, but also present an expanded structure with very limited resilience. Consequently, such stents are not deemed to be suitable for use in vessels that may be subject to high radially-compressive forces, such as the carotid arteries, which might abruptly collapse due to a sudden blow or other pressure to the neck.

Another design approach which has been practiced with plastically-deformable stents, with limited success to improve the longitudinal flexibility of the stent, is the use of expandable stent cells which are open, rather than closed. However, there is always been a difficult tradeoff between cell size and cell density, such that the relative ratio of metal struts in contact with the artery wall being supported cannot be reduced to the point that the stent either fails to provide adequate radial strength, or sufficient vascular wall coverage to prevent ingress of vascular tissue between the adjacent struts and into the vascular lumen (i.e., tissue prolapse).

For this reason, among others, self-expanding stents have been a primary focus for stent development for vascular applications with dynamic loading. Examples of such self-expanding stents include various mesh-like tubes (such as described in U.S. Pat. No. 4,655,771 to Wallsten), tubes formed of resilient materials (such as zig-zag stainless steel struts described in U.S. Pat. No. 4,580,568 to Gianturco), and tubes formed of superelastic shape memory materials such as nitinol (such as described in U.S. Pat. No. 6,306,141 to Jervis). However, self-expanding stents also suffers certain shortcomings. Mesh-like stents, as well as coiled and zig-zag stents described above, generally fail to provide a high degree of crush resistance or radial strength, and may tend to migrate from their initial deployment site. Additionally, the catheter delivery systems required for most self-expanding stents usually require a proximally-retractable constraining sheath, which tends to make the delivery systems larger in diameter and less flexible, thus limiting access to smaller vasculature and preventing treatment of more distal vascular blockages or lesions.

Significantly, a new type of stent prosthesis has been recently introduced, based upon the concept of a "bistable cell." The bistable cell is described in U.S. Pat. No. 6,488,702 to Besselink. The bistable cell comprises a first strut respectively joined at each of its ends to adjacent ends of a second strut which is relatively more flexible than the first, relatively rigid strut (e.g., the first strut can have a greater width than that of the second strut), thereby forming a closed cell which is defined by the enclosed area bounded by the first and second struts. The bistable cell design is such that it will operate as a spring between only two stable configurations, namely, a stable collapsed (unexpanded) configuration and a stable expanded configuration. A stent which is formed with conventional bistable cells will thus comprise a plurality of interconnected, closed bistable cells. When subjected to a radial force applied outwardly upon the interior surface of such a stent, the relatively flexible second strut will gradually deflect outwardly away from the more rigid first strut, until reaching a transition point where it will abruptly move in a spring-like fashion to a stable expanded position. Consequently, the bistable cell is unstable at any position intermediate the stable collapsed and expanded configuration.

Since this bistable cell is also collapsible by application of a force onto the outer surface of such a stent, directed in an inward radial direction, the stable expanded configuration can be reversibly moved into a stable collapsed configuration. Consequently, it is possible to practice this bistable cell design with much less regard to material properties, and generally permits the use of several metal alloys with varied properties of elasticity, elongation and tensile strength, such as stainless steel, cobalt alloys, nitinol alloys, and even polymers. Interestingly, this bistable cell design permits, for the first time, the ability of stents formed out of shape memory alloys such as nitinol to be crimped onto a balloon for retention until delivery to the vascular site. Since it is no longer necessary to use a delivery catheter provided with a retractable constraining sheath with retraction mechanisms for delivery of nitinol stents, it is now possible to deploy such bistable nitinol stents using catheters having a reduced profile and increased flexibility, and thus treat more tortuous anatomy and more distal lesions.

However, it has been generally been believed that the bistable cell design would optimally require a closed cell structure. Surprisingly, however, the present disclosure has proven that the full benefits of a bistable cell design can still be practiced with an open cell design, namely a cell which consist of at least two lobes within the cell boundary, wherein the multi-lobed open cell comprises more than a single pair of relatively rigid and relatively flexible struts. Consequently, this unique open-cell embodiment of the bistable cell provides significant improvement in the overall flexibility of the stent, thereby facilitation greater ease of catheter delivery into tortuous anatomy, as well as treatment of more difficult vascular conditions throughout the entire cardiovascular/peripheral system.

SUMMARY

Some embodiments disclosed herein are directed to an expandable stent structure, comprising a first relatively stiff portion with a dome-like structure having terminal inward hinges connected to two relatively flexible portions, that in turn are hinged in the opposite direction outward forming an inward apex into the cell and this continuation of the inward apex transitions to a relatively stiff structure ultimately connecting to another inverted dome-like long flexible portion. The stiff to flexible structure continues to alternate until a ring is formed. The inward pointing apex between the longer thick and thin alternating segments are designed to interact with each other during crimping and expansion to allow energy to be stored and released during transition points. In some embodiments, the stent can comprise a second relatively stiff portion having first and second ends and a second relatively flexible portion connected to the first and second ends of the first relatively stiff portion, and an opening formed through the first relatively stiff portion and the second relatively flexible portion such that the opening connects the first and second open areas, thereby creating first and second intermediate ends of the first relatively stiff portion and first and second intermediate ends of the second relatively flexible portion. The first relatively stiff portion and the first relatively flexible portion can substantially surround a first open area of the stent structure, and the first relatively stiff portion and the first relatively flexible portion can substantially surround a second open area of the stent structure. In some embodiments, the first intermediate end of the relatively stiff portion can be connected to the first intermediate end of the relatively flexible portion so as to create a first inward apex, and the second intermediate end of the relatively stiff portion can be connected to the second intermediate end of the relatively flexible portion so as to create a second inward apex. In some embodiments, the stent structure can be configured such that, in a collapsed configuration, the first inward apex can be in contact with the second inward apex and, in an expanded configuration, the first inward apex can be biased to move in a first circumferential direction and the second inward apex can be biased to move in a second circumferential direction that can be different than the first circumferential direction.

Some embodiments disclosed herein are directed to an expandable stent structure, comprising a first relatively stiff portion having first and second ends and a first relatively flexible portion connected to the first and second ends of the first relatively stiff portion, a second relatively stiff portion having first and second ends and a second relatively flexible portion connected to the first and second ends of the first relatively stiff portion, and an opening formed through the first relatively stiff portion and the second relatively flexible portion such that the opening connects the first and second open areas, thereby creating first and second intermediate ends of the first relatively stiff portion and first and second intermediate ends of the second relatively flexible portion. The first relatively stiff portion and the first relatively flexible portion can substantially surround a first open area of the stent structure, and the first relatively stiff portion and the first relatively flexible portion can substantially surround a second open area of the stent structure. In some embodiments, the first intermediate end of the relatively stiff portion can be connected to the first intermediate end of the relatively flexible portion so as to create a first inward apex, and the second intermediate end of the relatively stiff portion can be connected to the second intermediate end of the relatively flexible portion so as to create a second inward apex. In some embodiments, the stent structure can be configured such that, in a collapsed configuration, the first inward apex can be in contact with the second inward apex and, in an expanded configuration, the first inward apex can be biased to move in a first circumferential direction (at least during the initial portion or phase of expansion) and the second inward apex can be biased to move in a second circumferential direction (at least during the initial portion or phase of expansion) that can be different than the first circumferential direction.

Some embodiments disclosed herein are directed to an expandable stent structure, comprising a first relatively stiff portion having first and second ends and a first relatively flexible portion connected to the first and second ends of the first relatively stiff portion, the first relatively stiff portion and the first relatively flexible portion substantially surrounding a first open area of the stent structure, a second relatively stiff portion having first and second ends and a second relatively flexible portion connected to the first and second ends of the first relatively stiff portion, the first relatively stiff portion and the first relatively flexible portion substantially surrounding a second open area of the stent structure, and an opening formed through the first relatively stiff portion and the second relatively flexible portion such that the opening connects the first and second open areas, thereby creating first and second intermediate ends of the first relatively stiff portion and first and second intermediate ends of the second relatively flexible portion.

In some embodiments, the first intermediate end of the relatively stiff portion can be connected to the first intermediate end of the relatively flexible portion so as to create a first inward apex, and the second intermediate end of the relatively stiff portion can be connected to the second intermediate end of the relatively flexible portion so as to create a second inward apex. The first inward apex can have a shape that can be different than a shape of the second inward apex.

Some embodiments disclosed herein are directed to a lumen support having a plurality of stable configurations, the lumen support comprising one or more open cells, each open cell comprising a first strut having a first and a second end portion, a second strut having a first and a second end portion, a first pair of half struts positioned between the first and second full struts, the first pair of half struts defining a first inward facing apex, and a second pair of half struts positioned between the first and second full struts, the second pair of half struts defining a second inward facing apex that can be adjacent to the first inward facing apex. In some embodiments, the inward facing apices can each define an angled surface, and the angle of the angled surface of the first inward facing apex can be parallel to the angle of the angled surface of the second inward facing apex. In some embodiments, each open cell can be configured to move between at least a first stable collapsed configuration and a first stable expanded configuration, there being no stable configurations between the first stable collapsed configuration and the first stable expanded configuration. In some embodiments, the lumen support can be configured such that, in a collapsed state, the inward apices are abutting and in an expanded state, the end portions move in opposite circumferential directions (at least during the initial portion or phase of expansion).

Some embodiments disclosed herein are directed to a lumen support having a plurality of stable configurations, the lumen support comprising one or more open cells, each open cell comprising a first strut having a first and a second end portion, a second strut having a first and a second end portion, a first pair of half struts positioned between the first and second full struts, the first pair of half struts defining a first inward facing apex, and a second pair of half struts positioned between the first and second full struts, the second pair of half struts defining a second inward facing apex that can be adjacent to the first inward facing apex. In some embodiments, the inward facing apices can each define an angled surface. In some embodiments, a portion of the second inward facing apex can longitudinally overlap a portion of the first inward facing apex when the open cell can be in a collapsed position.

Some embodiments disclosed herein are directed to a method of supporting a passageway with an expandable structure, wherein the expandable structure can comprise a first inward facing apex, a second inward facing apex, the second inward facing apex that can be adjacent to but oppositely oriented relative to the first inward facing apex when the expandable structure is in a collapsed configuration, and a first member and a second member surrounding the first and second inward facing apices. In some embodiments, the method can comprise positioning the expandable structure in a passageway in a collapsed configuration and radially expanding the expandable structure and thereby moving the first inward facing apex in a first circumferential direction (at least during the initial portion or phase of expansion) and moving the second inward facing apex in a second circumferential direction (at least during the initial portion or phase of expansion) that is different than the first circumferential direction.

Further advantages and embodiments will become evident from the attached drawings.

BRIEF DESCRIPTION OF THE DRAWINGS

In the drawings:

FIGS. 2A and 2B show an exemplary expandable device according to various aspects of the disclosure;

DETAILED DESCRIPTION

Figure 1B:
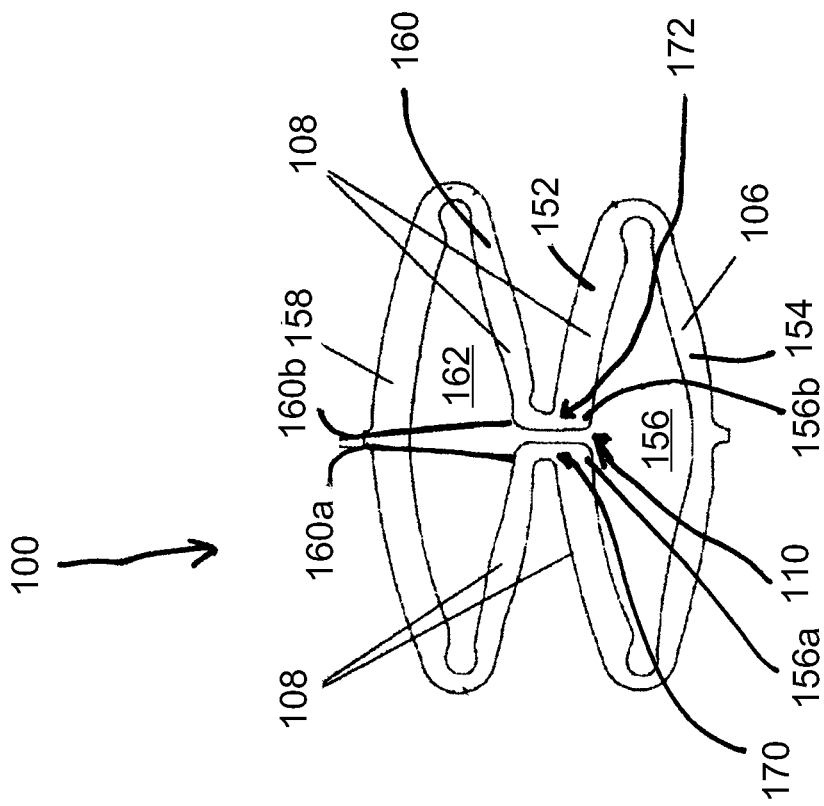
FIGS. 1A and 1B show an exemplary expandable device according to various aspects of the disclosure.
Figure 1A:
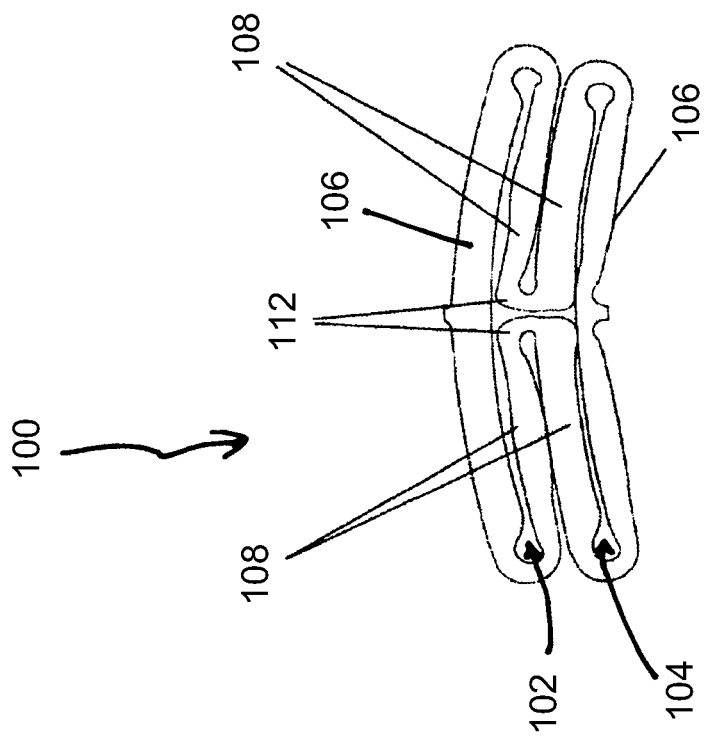

The embodiments described herein relate to expandable devices 100, such as, for example, stents, other medical devices, and other medical and non-medical lumen support devices, having open cells. In some embodiments, the devices can be configured for release of stored energy during expansion related to eversion of the coapted dome and crimping when the inward apices coapt and move though an inversion point. The open cells are illustrated in FIGS. 1A and 1B. FIG. 1A illustrates two cells 102, 104 of an open cell arrangement in a collapsed state, the open cell segment having two full struts 106 and four half struts 108. FIG. 1B illustrates the open cell of FIG. 1A in an expanded state.

The cells illustrated in FIGS. 1A and 1B are referred to as "open" cells because of the gap 110 formed between the end portions 112 of the half struts 108 of each cell. This gap 110 is an opening between the two cells 102, 104. In contrast, closed cell arrangements typically include arrangements where each cell includes a complete closed periphery around an open area. If the gap were closed in FIGS. 1A and 1B, the segment would include two closed cells. For example, the cells of FIGS. 5B and 6 of U.S. Pat. No. 6,488,702 illustrate closed cells. The U.S. Pat. No. 6,488,702 is hereby incorporated by reference as if fully set forth herein.

In the collapsed state (as in FIG. 1A), the end portions 112 of the half struts 108 can interact (or coaptate) when an additional compressive force is exerted on the stent such that the stent cell is able to be collapsed to a greater degree. This can beneficially decrease the profile diameter of a stent comprising a plurality of open cells. Coaptation between the end portions of the half struts occurs when the end portions of the half struts are forced into contact with one another by radially compressing the stent so that they are "locked" or engaged together enabling the stent to be collapsed to a greater extent. The coaptation essentially reduces the amount of spring back or recoil of the cell when the radially compressive external force is removed.

For example, referring to FIG. 1A, the expandable, bistable open cell design incorporates the following features:

a first relatively stiff portion (152) having first and second ends and a first relatively flexible portion (154) connected to the first and second ends of the first relatively stiff portion, the first relatively stiff portion and the first relatively flexible portion substantially surrounding a first open area (156) of the stent structure;

a second relatively stiff portion (158) having first and second ends and a second relatively flexible portion (160) connected to the first and second ends of the first relatively stiff portion, the first relatively stiff portion and the first relatively flexible portion substantially surrounding a second open area (162) of the stent structure; and an opening (110) formed through the first relatively stiff portion and the second relatively flexible portion such that the opening connects the first and second open areas, thereby creating first and second intermediate ends (152a, 152b) of the first relatively stiff portion and first and second intermediate ends (160a, 160b) of the second relatively flexible portion;

wherein:

the first intermediate end (152a) of the relatively stiff portion is connected to the first intermediate end (160a) of the relatively flexible portion so as to create a first inward apex (170), the second intermediate end (152b) of the relatively stiff portion is connected to the second intermediate end (160b) of the relatively flexible portion so as to create a second inward apex (172), and the stent structure is configured such that, in a collapsed configuration, the first inward apex (170) is in contact with the second inward apex (172) and, in an expanded configuration, the first inward apex is biased to move in a first circumferential direction and the second inward apex is biased to move in a second circumferential direction that is different than the first circumferential direction.

FIG. 2A illustrates an additional embodiment of an open cell structure 200. In particular, two connected open cells 202, 204 are shown in FIG. 2A, with the cells being shown in the as manufactured state (i.e., before being crimped onto the delivery apparatus). FIG. 2B is an enlargement of a portion of the open cells in FIG. 2A, defined by the dashed rectangle.

With reference to FIG. 2B, the end portion 226, 228 of each pair of the respective thin struts 216 and thick struts 218 defines an angled surface, i.e., the first angled surface 222 and second angled surface 224. In some embodiments, the gap 210 between the first angled surface 222 and the second angle surface 224 can allow the open cells 202, 204 to collapse to a greater extent when they are crimped onto the stent delivery apparatus. Additionally, the first and second angled surfaces 224, 226 can be angled to control the direction that the respective end portions move during at least during the initial portion or phase of expansion of the open cells, thereby increasing predictability and repeatability of the struts and cells during cell expansion.

In particular, the angle of the first and second angled surfaces 222, 224 in the embodiment shown in FIG. 2B can cause the first end portion 226 to move in the direction indicated by arrow A1, at least during the initial portion or phase of expansion. Further, in some embodiments, portions of the first angled surface 222 or the second angled surface 224 can be configured to longitudinally overlap portions of the second angled surface 224 or the first angled surface 222, respectively, at least when the open cell is in a collapsed configuration. For example, with reference to FIG. 2B, the second angled surface 224 can have a more pronounced second end portion 228 that overlaps the first angled surface at least when the open cell is in a collapsed configuration. In some embodiments, the increased angle of the second angled surface 224 can improve the ability of the first angled surface 222 of the first end portion 226 to slip off of the second angled surface 224 during expansion of the open cells.

Further, the angles of the first and second angled surfaces 222, 224 can be configured to contribute to a reduction in recoil or spring back of the stent when the stent is crimped on the stent delivery device. In particular, the end portions 226, 228 releasably engage with or coaptate against one another (as mentioned above) when crimped so that such end portions are releasably held together by the friction and tensile forces of each of the end portions so that such end portions are inhibited from moving apart, thereby holding the cells in a more collapsed position or state.

Figure 3A:
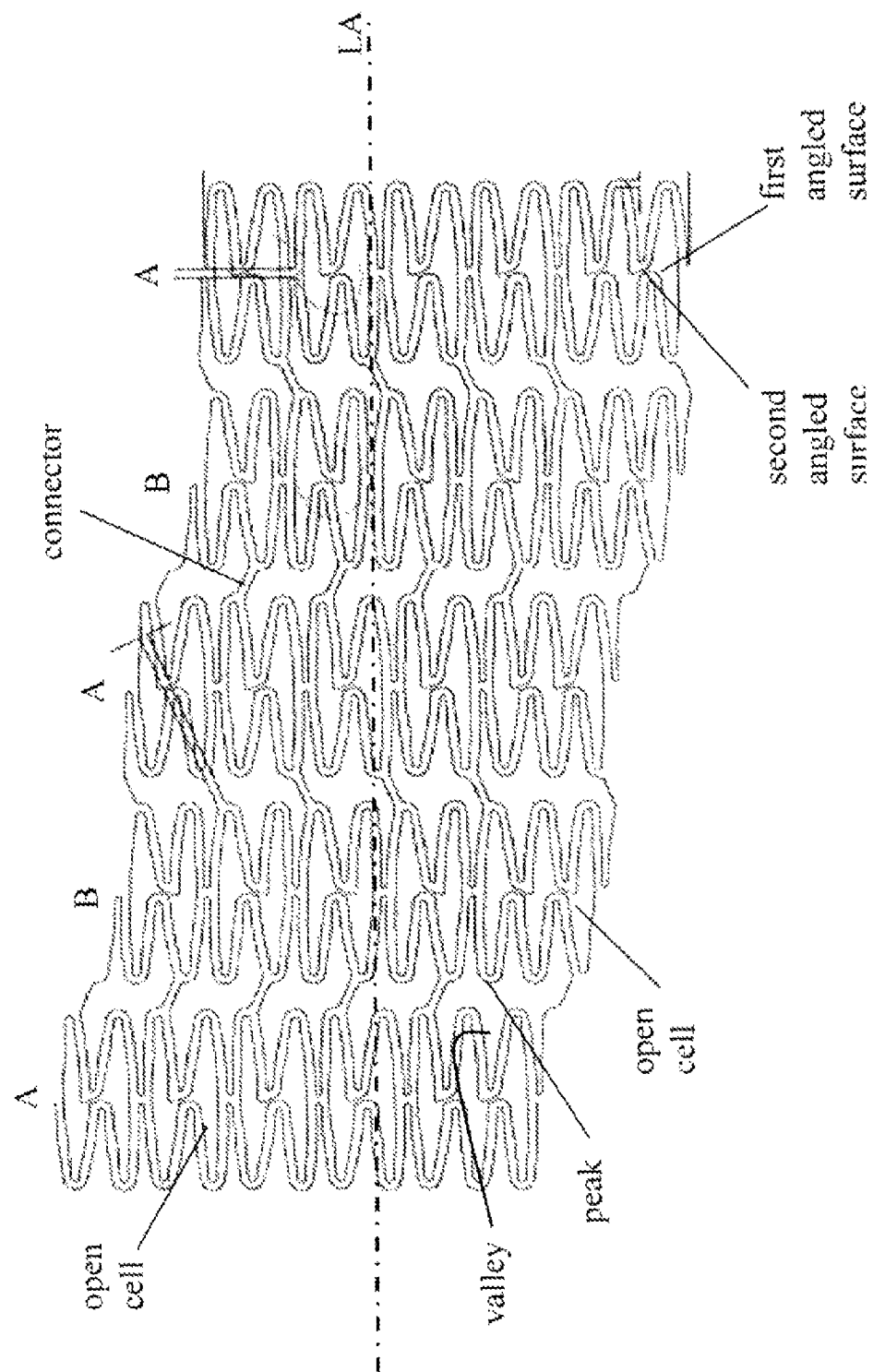
FIGS. 3A and 3B show an exemplary expandable device consistent with various aspects of the disclosure.

FIG. 3A is a plan view of the manufacturing pattern for another embodiment of a stent. In some embodiments, the stent embodiment illustrated in FIG. 3A can have one or more first annular segments A and one or more second annular segments B longitudinally arranged in an alternating pattern. The annular segments A, B can comprise a plurality of open cells and can be connected to adjacent annular segments A, B with one or more connectors. The open cells illustrated can have any of the same shapes, features, elements, or other details of any of the other cells disclosed herein.

In some embodiments, as illustrated, the cells and/or segments A, B can be circumferentially offset relative to one another. For example, with reference to FIG. 3A, one or more of the open cells in segment B can be positioned so that a peak of one or more (or all) of the open cells is generally aligned with a valley of one or more (or all) of the open cells of Segment A. Alternatively (not illustrated), the cells and/or segments A, B can be generally circumferentially aligned relative to one another so that, for example, the peaks of segment A generally align with the peaks of segment B.

The connectors of this embodiment or any other embodiment disclosed herein can be linear, curved, severable, substantially non-severable or otherwise, or can comprise any combination of linear, curved, or angled portions or elements. As illustrated, the connectors have a linear shape, and can be arranged to define an obtuse angle relative to a longitudinal axis LA defined by the stent. Further, the connectors can be arranged so as to connect with the open cells at positions or points that are not directly on the center of the peaks or apices of the open cells. Stated another way, the connectors can be positioned off-peak. In some embodiments, the connectors can be positioned at the peak of the apices. In some embodiments, the connectors can have a linear shape and can be arranged so as to be generally parallel with the longitudinal axis LA of the stent.

Also, with reference to FIG. 3A, similar to some other stent embodiments disclosed herein, in some embodiments, the second angled surface can project in an axial direction to a greater extent than the first angled surface so as to longitudinally overlap the first end portion to a greater extent as compared to the overlap provided by the first end portion or first angle surface. Additionally, in some embodiments, the orientation of the second angled surface relative to the first angled surface can alternate from one segment A, B to the next (as illustrated), or from one cell to the next.

Figure 3B:
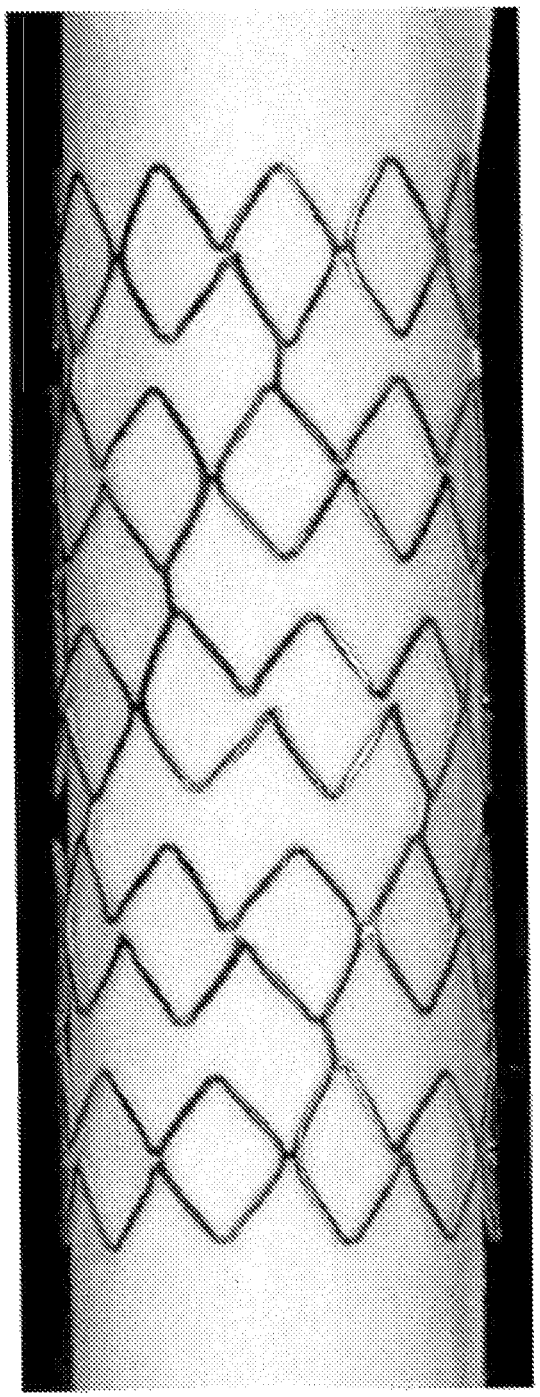

FIG. 3B illustrates a stent embodiment having the pattern illustrated in FIG. 3A, showing the stent in an expanded state.

Figure 4A:
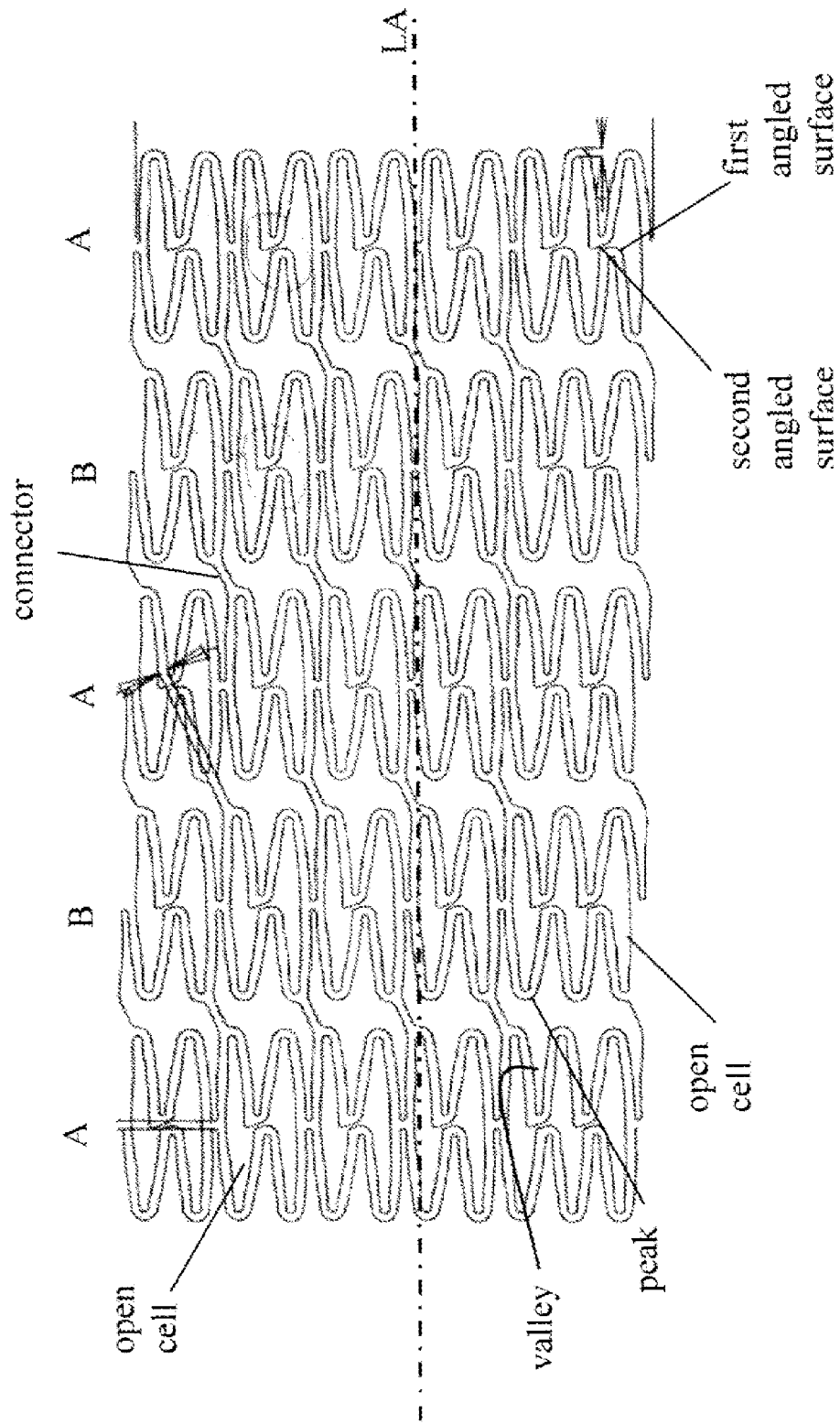
FIGS. 4A and 4B show an exemplary expandable device consistent with various aspects of the disclosure.

FIG. 4A is a plan view of the manufacturing pattern for another embodiment of a stent. In some embodiments, the stent embodiment illustrated in FIG. 4A can have one or more annular segments A, B longitudinally arranged in an alternating pattern. The annular segments A, B can comprise a plurality of open cells and can be connected to adjacent annular segments A, B with one or more connectors. In contrast with the stent embodiment illustrated in FIGS. 3A, 3B, the open cells can be similarly configured and similarly oriented from one segment A, B to the next segment A, B. The open cells illustrated can have any of the same shapes, features, elements, or other details of any of the other cells disclosed herein.

In some embodiments, as illustrated, the linearly adjacent cells and/or segments A can be circumferentially offset relative to one another. For example, with reference to FIG. 4A, one or more of the open cells in segment B can be positioned so that a peak of one or more (or all) of the open cells is slightly circumferentially offset with respect to an adjacent peak of one or more (or all) of the open cells of Segment A. Alternatively (not illustrated), the cells and/or segments A, B can be generally circumferentially aligned relative to one another so that, for example, the peaks of segment A generally align with the peaks of segment B.

The connectors can be linear, curved, or otherwise, or can comprise any combination of linear, curved, or angled portions or elements. As illustrated, the connectors have a linear shape, and can be arranged to define an obtuse angle relative to a longitudinal axis LA defined by the stent. Further, the connectors can be arranged so as to connect with the open cells at positions or points that are not directly on the center of the peaks or apices of the open cells. Stated another way, the connectors can be positioned off-peak. In some embodiments, the connectors can be positioned at the peak of the apices. In some embodiments, the connectors can have a linear shape and can be arranged so as to be generally parallel with the longitudinal axis LA of the stent.

Also, with reference to FIG. 4A, similar to some other stent embodiments disclosed herein, in some embodiments, the second angled surface can be project in an axial direction to a greater extent than the first angled surface so as to longitudinally overlap the first end portion to a greater extent as compared to the overlap provided by the first end portion or first angle surface. Additionally, in some embodiments, the orientation of the second angled surface relative to the first angled surface can alternate from one segment A, B to the next (as illustrated), or from one cell to the next.

Figure 4B:
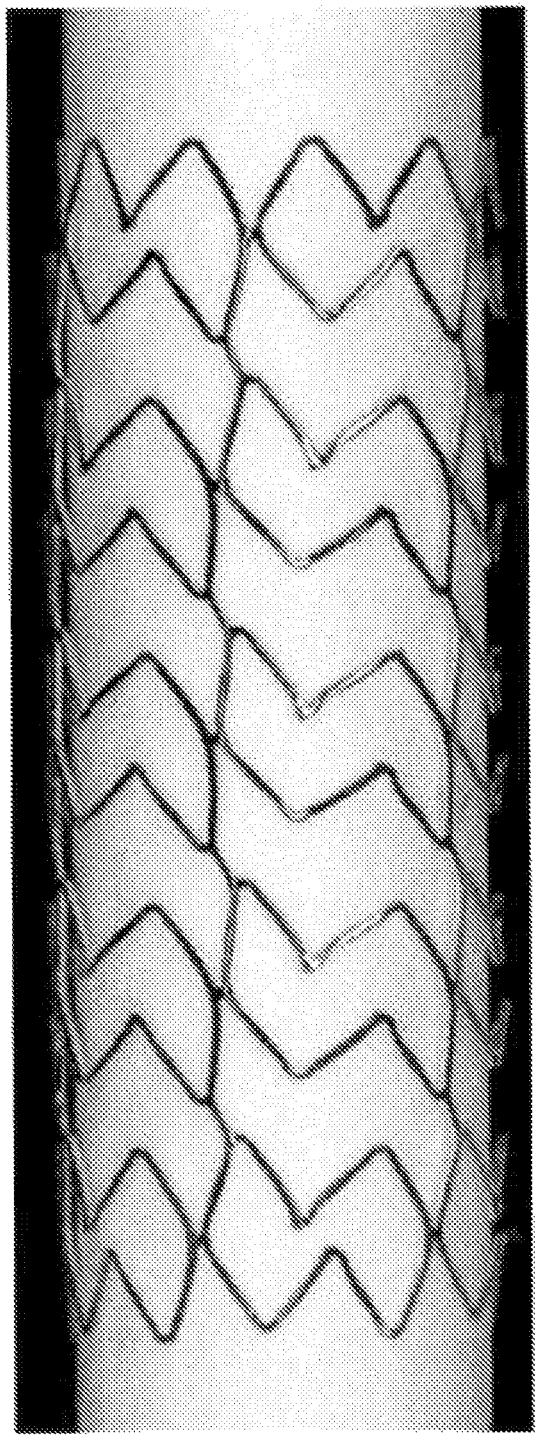

FIG. 4B illustrates a stent embodiment having the pattern illustrated in FIG. 4A, showing the stent in an expanded state. As can be seen, the stent embodiment illustrated in FIG. 4B can be expanded so that the connectors and some of the struts generally align in a spine like arrangement.

Additionally, one or more of the cells of any of the embodiments disclosed herein can be configured to have (without limitation) bistable or transition point technology (also referred to as inflection point), as described in U.S. Pat. No. 6,488,702. Briefly stated, in such embodiments, each cell can have at least one rigid strut and one more-flexible strut (i.e., one thick strut and one thin strut). The cell can be configured such that the end points of the flexible, thin strut(s) are substantially constrained such that the thin strut is caused to expand through an inflection point that permits the thin strut to self-expand (or be expanded with a lesser force) from the inflection point to a stable expanded state.

In particular, with reference to FIG. 1A, the portion of the thin strut facing the open area of each cell has a convex shape in the collapsed state, and has a concave shape in the expanded state (shown in FIG. 1B). Between the collapsed, convex shape and the expanded, concave shape, the flexible strut passes through the inflection point at which point the thin strut requires a reduced force to further expand to the expanded state.

Figure 5:
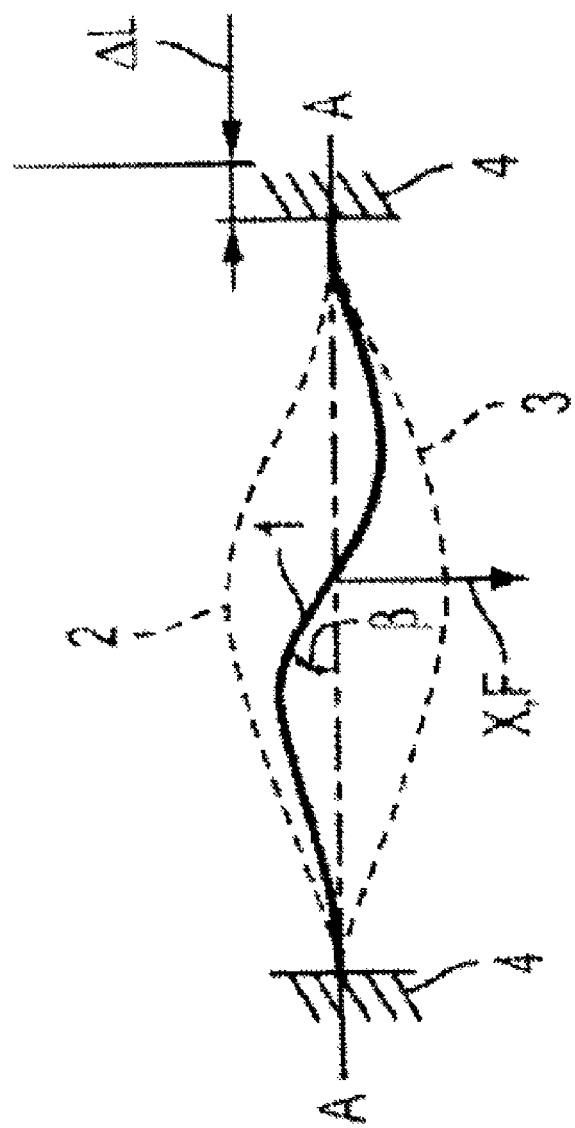
FIG. 5 shows an exemplary prior art bi-stable cell.

This is shown schematically in FIG. 5 (which is FIG. 1B from the '702 patent, which is incorporated by reference herein). Here, a force F is applied to the strut to change it from the convex position (position 2) to the concave position (position 3). The solid line position of the strut (i.e., position 1) shows the strut at approximately the inflection point position where any additional force will cause the strut to continue to expand automatically or with reduced force to position 3. All positions between position 2 and position 3 are unstable.

A stent having a plurality of these open cells arranged in a circumferential direction can be expanded from a stable collapsed state using an expansion balloon or other expansion means through the inflection point after which the stent cells will expand to the stable expanded state with little or no force. The cell can then be plastically deformed to a second expanded state that has a larger size than the stable expanded state. Additionally, the stent can be plastically collapsed from the stable collapsed state to a second collapsed state by exerting a radial force on the stent when the stent is in the stable collapsed state, so that the profile of the stent is even smaller.

Certain embodiments described herein are directed to systems, methods, and apparatuses to treat stenosis, lesions, or other defects in blood vessels, including, but not limited to, the aorta, iliac arteries or veins, coronary arteries, femoral arteries, thoracic arteries, and/or the superficial femoral artery, to name a few. However, the systems, methods, and apparatuses may have application to other vessels or areas of the body such as biliary vessels or ducts, or to other fields, and such additional applications are intended to form a part of this disclosure. And, while specific embodiments may be described herein with regard to particular portions of a person's vasculature, it is to be understood that the embodiments described can be adapted for use in other portions of a person's or animal's vasculature or other portions of the body and are not limited to the specific blood vessels specified herein.

Although the inventions have been disclosed in the context of a certain preferred embodiments and examples, it will be understood by those skilled in the art that the present inventions extend beyond the specifically disclosed embodiments to other alternative embodiments and/or uses of the inventions and obvious modifications and equivalents thereof. In addition, while a number of variations of the inventions have been shown and described in detail, other modifications, which are within the scope of the inventions, will be readily apparent to those of skill in the art based upon this disclosure. It can be also contemplated that various combinations or subcombinations of the specific features and aspects of the embodiments may be made and still fall within the scope of the inventions. For example, in some embodiments, the features, configurations, or other details disclosed or incorporated by reference herein with respect to some of the connector or stent embodiments are combinable with other features, configurations, or details disclosed herein with respect to other connector or stent embodiments to form new embodiments not explicitly disclosed herein. All of such embodiments having combinations of features and configurations are contemplated as being part of this disclosure. Additionally, unless otherwise stated, no features or details of any of the stent or connector embodiments disclosed herein are meant to be required or essential to any of the embodiments disclosed herein, unless explicitly described herein as being required or essential.

It will be apparent to those skilled in the art that various modifications and variations can be made to the expandable devices of the present disclosure without departing from the scope of the invention. Throughout the disclosure, use of the terms "a," "an," and "the" may include one or more of the elements to which they refer. Other embodiments of the invention will be apparent to those skilled in the art from consideration of the specification and practice of the invention disclosed herein. It is intended that the specification and examples be considered as exemplary only.

What is claimed is:

1. A method of supporting a passageway with an expandable structure, comprising:
   positioning the expandable structure in a passageway in a collapsed configuration, the expandable structure comprising:
      a first inward facing apex having an angled surface,
      a second inward facing apex having an angled surface, the second inward facing apex being adjacent to but oppositely oriented relative to the first inward facing apex when the expandable structure is in a collapsed configuration, and
      a first member and a second member surrounding the first and second inward facing apices; and
   radially expanding the expandable structure and thereby moving the first inward facing apex in a first circumferential direction and moving the second inward facing apex in a second circumferential direction that is different than the first circumferential direction, wherein an angle of the angled surface of the second inward facing apex is greater than an angle of the angled surface of the first inward facing apex.

2. A lumen support having a plurality of stable configurations, the lumen support comprising:
   one or more open cells, each open cell comprising:
   a first strut having a first and a second end portion,
   a second strut having a first and a second end portion,
   a first pair of half struts positioned between the first and second full struts, the first pair of half struts defining a first inward facing apex, and
   a second pair of half struts positioned between the first and second full struts, the second pair of half struts defining a second inward facing apex that is adjacent to the first inward facing apex,
   wherein:
      the inward facing apices each define an angled surface, and
      the angle of the angled surface of the second inward facing apex is greater than the angle of the angled surface of the first inward facing apex.

3. The lumen support of claim 2, wherein each open cell is configured to move between at least a first stable collapsed configuration and a first stable expanded configuration, there being no stable configurations between the first stable collapsed configuration and the first stable expanded configuration.

4. The lumen support of claim 2, wherein the lumen support is configured such that, in a collapsed state, the inward apices are abutting and in an expanded state, the end portions move in opposite circumferential directions.

5. The lumen support of claim 2, further comprising one or more annular segments (A) comprising the one or more open cells and one or more annular segments (B) comprising the one or more open cells.

6. The lumen support of claim 5, wherein the one or more annular segments (A) are longitudinally arranged in an alternating pattern with one or more annular segments (B).

7. The lumen support of claim 6, wherein the one or more annular segments (A) are connected to adjacent annular segments (B) with one or more connectors.

8. The lumen support of claim 7, wherein the one or more connector is chosen from linear, curved, severable, or non-severable.

9. The lumen support of claim 5, wherein the one or more annular segments (A) are circumferentially offset relative to the one or more annular segments (B).

10. The lumen support of claim 2, wherein the angled surface of the second inward facing apex projects in an axial direction to a greater extent than the angled surface of the first inward facing apex.

11. A lumen support having a plurality of stable configurations, the lumen support comprising:
    one or more open cells, each open cell comprising:
       a first strut having a first and a second end portion,
       a second strut having a first and a second end portion,
       a first pair of half struts positioned between the first and second full struts, the first pair of half struts defining a first inward facing apex having a first angled surface and
       a second pair of half struts positioned between the first and second full struts, the second pair of half struts defining a second inward facing apex having a second angled surface, wherein the second inward facing apex is adjacent to the first inward facing apex,
    wherein:
       the second angled surface projects in an axial direction to a greater extent than the first angled surface.

12. The lumen support of claim 11, further comprising one or more annular segments (A) comprising the one or more open cells and one or more annular segments (B) comprising the one or more open cells.

13. The lumen support of claim 12, wherein the one or more annular segments (A) are longitudinally arranged in an alternating pattern with one or more annular segments (B).

14. The lumen support of claim 13, wherein the one or more annular segments (A) are connected to adjacent annular segments (B) with one or more connectors.

15. The lumen support of claim 12, wherein the one or more annular segments (A) are circumferentially offset relative to the one or more annular segments (B).

16. A method of supporting a passageway with an expandable structure, comprising:
    positioning the expandable structure in a passageway in a collapsed configuration, the expandable structure comprising:
       a first inward facing apex having a first angled surface,
       a second inward facing apex having a second angled surface, the second inward facing apex being adjacent to but oppositely oriented relative to the first inward facing apex when the expandable structure is in a collapsed configuration, and
       a first member and a second member surrounding the first and second inward facing apices; and
    radially expanding the expandable structure and thereby moving the first inward facing apex in a first circumferential direction and moving the second inward facing apex in a second circumferential direction that is different than the first circumferential direction;

wherein an angle of the second angled surface is greater than an angle of the first angled surface of the first inward facing apex.

\* \* \* \* \*